US006497139B1

(12) United States Patent
Locatelli

(10) Patent No.: US 6,497,139 B1
(45) Date of Patent: Dec. 24, 2002

(54) METHOD FOR CHARACTERIZING A POROUS PERMEABLE MEDIUM BY POLARIZED GAS NMR

(75) Inventor: Marcel Locatelli, Montbonnot (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/486,537

(22) PCT Filed: Jul. 8, 1999

(86) PCT No.: PCT/FR99/01662

§ 371 (c)(1),
(2), (4) Date: Aug. 1, 2000

(87) PCT Pub. No.: WO00/03261

PCT Pub. Date: Jan. 20, 2000

(30) Foreign Application Priority Data

Jul. 10, 1998 (FR) .............................. 98 08921

(51) Int. Cl.[7] .................... G01R 33/44; G01N 15/08; G01N 24/08; G01N 33/46
(52) U.S. Cl. .......................... 73/38; 324/307
(58) Field of Search .............................. 73/38; 324/306, 324/307

(56) References Cited

U.S. PATENT DOCUMENTS

| 3,850,040 A | 11/1974 | Orr, Jr. et al. |
| 5,285,688 A | 2/1994 | Robbins et al. |
| 5,309,098 A | 5/1994 | Coates et al. |
| 5,357,063 A | 10/1994 | House et al. |
| 5,610,522 A | 3/1997 | Locatelli et al. |

OTHER PUBLICATIONS

Gregory et al., "Pore–Structure Determinations of Silica Aerogels by $^{129}$Xe NMR Spectroscopy and Imaging," *Journal of Magnetic Resonance*, Apr. 1998, Academic Press, USA, vol. 131, No. 2, pp 327–335.

Mansfield et al., "The Use of $^{129}$Xe NMR Exchange Spectroscopy for Probing the Microstructure of Porous Materials," *Chemical Physics Letter*, Oct. 1, 1993, Netherlands, vol. 213, No. 1–2, pp 153–157.

(List continued on next page.)

*Primary Examiner*—Daniel S. Larkin
(74) *Attorney, Agent, or Firm*—Harness, Dickey & Pierce

(57) ABSTRACT

The invention involves the characterization of a permeable porous object. It involves the following steps:
 placing the object in an air-tight container,
 creating a partial vacuum in the container containing the aforesaid object,
 measuring the residual pressure in the container in which the partial vacuum is formed,
 introducing a quantity of polarized gas into the container in partial vacuum,
 measuring the residual pressure in the container after introduction of the aforesaid quantity of polarized gas,
 determination of the density of the polarized gas introduced into the container from the aforesaid pressure measurements,
 NMR measurement of the mass quantity of polarized gas contained in a known volume of the object placed in the air-tight container,
 determination of the porosity of the object by calculation of the ratio of the mass quantity of polarized gas to the density of the polarized gas introduced into the container.

22 Claims, 1 Drawing Sheet

OTHER PUBLICATIONS

Pasquier et al., "$^{129}$Xe NMR as a Probe of the Dynamics of Gas Confined in Porous Vycor," Third International Meeting on Recent Advances in MR Applications to Porous Media, Louvain La Neuve, Belgium, Sep. 3–6, 1995, *Magnetic Resonance Imaging*, 1996 Elsevier, USA, vol. 14, No. 7–8, pp 971–973.

Leduc et al., "Voir Les Poumons GRÂce A L'Hélium," *La Recherche* 287, May 1996, pp 41–43.

Durrasse et al., "Low–Field $^3$He Nuclear Magnetic Resonance in Human Lungs," *C.R. ACAD. Sci.*, Paris, t. 324, Série II b, 1997, pp 691–700.

METHOD FOR CHARACTERIZING A POROUS PERMEABLE MEDIUM BY POLARIZED GAS NMR

FIELD OF THE INVENTION

This invention concerns the characterization of porous permeable media, for example wood objects attacked by parasites.

STATE OF THE PRIOR ART

It is known, from document U.S. Pat. No. 5,357,063 for example, that acoustic energy can be used to detect and identify objects buried in the ground. Acoustic energy is injected into the soil and a reflected signal is received and processed to produce a image which is representative of the reflected energy. This technique, which is applied in particular for detection of buried objects, is useful for not very porous media. If the medium examined is too porous, there are problems of propagation of the acoustic energy which affects the accuracy of the method.

U.S. Pat. No. 5,285,688 also involves an acoustic method. It discloses a system for detection of wood-destroying insects, in particular a system which detects acoustic emissions produced by these insects and which reveals their presence. This system is based on listening to active insects and consequently requires the presence of living insects. This is not always the case for media to be characterized.

A porous permeable medium may also be characterized by methods involving impregnating a medium with a dense liquid, such as mercury, or with water. These methods require the presence of a liquid. They are thus more particularly applicable to areas where a liquid is already present in the media in question, for example in the field of drilling (see patents U.S. Pat. No. 5,309,098 and U.S. Pat. No. 5,610,522). In other areas of application such as those involving works of art, there is a risk of deterioration of the medium to be characterized.

To avoid the presence of a liquid, NMR imaging using the resonance of helium 3 has been used to visualize for example the porosity of lungs. This technique was disclosed in the following articles:

"Voir les poumons grace a l'helium" (See the lungs using helium) by M. Leduc and E. Otten, in the review La Recherche n° 287, May 1996, pages 41–43;

"Low-field $^3$He nuclear magnetic resonance in human lungs" by L. Darrasse, G. Guillot, P. J. Nacher and G. Tastevin, C.R. Acad. Sci. Paris, t. 324, series IIb, p. 691–700, 1997.

It involves having a patient inhale polarized helium 3 and visualizing the gas inhaled by nuclear magnetic resonance. In this technique, high resolution imagery must be done to measure the porosity from the measurement of the pore dimensions on the images, thus requiring complex and costly experimental means.

SUMMARY OF THE INVENTION

To overcome the drawbacks of the prior art, a method for characterization is proposed using NMR of polarized gases, such as $^3$He or $^{129}$Xe. The invention thus involves a method for characterizing a porous permeable object including the following steps:

placing the object in an air-tight container, creating a partial vacuum in the container containing the aforesaid object, measuring the residual pressure in the container in which the partial vacuum is formed, introducing a quantity of polarized gas in the container in partial vacuum, measuring the pressure in the container after introduction of the aforesaid quantity of polarized gas, determination of the density of the polarized gas introduced into the container from the aforesaid pressure measurements, NMR measurement of the mass quantity of polarized gas contained in a known volume of the object placed in the air-tight container, determination of the porosity of the object by calculation of the ratio of the mass quantity of polarized gas to the density of the polarized gas introduced into the container.

The object can be placed in a rigid container. It could also be a container sufficiently flexible so that the depressurizing provokes adherence of the container to the object. The quantity of polarized gas introduced in the container may then be such that the container continues to adhere to the object.

The polarized gas could be $^3$He or $^{129}$Xe.

The NMR measurement can be done by a NMR area system. This measurement can be done by a NMR area system involving CMPG sequences, thus allowing for determination of medium porosity dimensions.

The NMR measurement can also be done by a NMR volume system.

The invention also involves a device for characterizing a porous permeable object including:

an air-tight container apt to receive the aforesaid object, means for measurement of the pressure in the air-tight container, means for depressurizing the aforesaid air-tight container, means for introducing a quantity of polarized gas into the depressurized air-tight container, means for NMR measurement of the mass quantity of polarized gas contained in a known volume of the object placed in the air-tight container, means for determination of the density of the polarized gas introduced in the container from data supplied by the means of measurement and determination of the porosity of the object from measurement of the mass quantity of the polarized gas and the density of the polarized gas introduced into the container.

BRIEF DESCRIPTION OF THE DRAWINGS

The invention will be better understood and the other advantages and particular aspects will be clearer with the reading of the following description, provided as a non-limiting example, accompanied by the appended figures among which.

DETAILED DESCRIPTION OF EMBODIMENTS OF THE INVENTION

Figure 1:
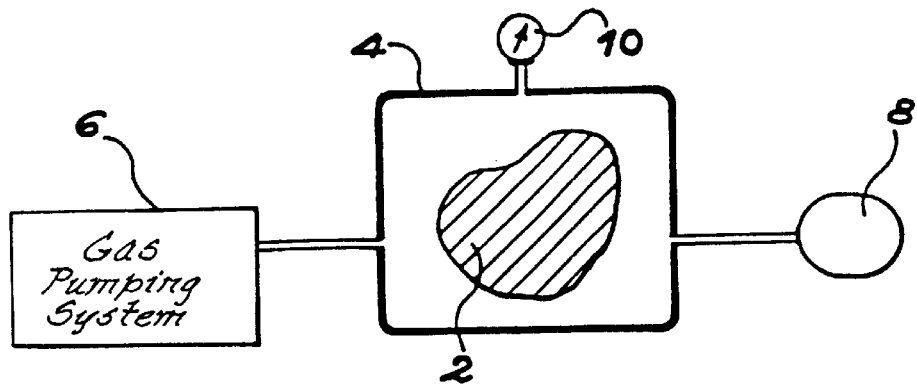
FIG. 1 illustrates a device for characterizing a porous permeable object according to this invention and including an air-tight rigid container.

According to the invention, the polarized gas is introduced into the object to be characterized at a controlled pressure. For this, and as shown in FIG. 1, the object 2 is placed in an air-tight container 4 linked to a gas pumping system 6 and to a polarized gas tank 8. A manometer 10 is used to measure the pressure within the air-tight container 4.

In the embodiment shown in FIG. 1, the air-tight container 4 is rigid.

The polarized gas used is for example $^3$He which is polarized by a known method (see for example the article cited above by M. Leduc and E. Otten).

The NMR measurement is made in a known volume of the object from, for example, an area system such as that described in patent U.S. Pat. No. 5,610,522. This measurement determines the mass quantity of gas contained in this volume of the object.

After placing the object 2 in the air-tight container 4, a partial vacuum is created in the container. Once the container has been depressurized, the residual pressure is measured with the manometer 10. Polarized gas from the tank 8 is then introduced into the air-tight container 4. The pressure within the container 4 is then measured. The density of the polarized gas present within the air-tight container can be derived from the difference between the pressure after introduction of the polarized gas and the residual pressure.

From the mass quantity obtained by NMR measurement and the density of the polarized gas, the volume of the polarized gas in the object and the average porosity in the measurement volume can be determined.

The air-tight container may be rigid or flexible. The use of a flexible container makes it possible to limit the volume of polarized gas to be introduced to obtain a given gas pressure. Since the NMR signal received is proportional to the gas density, it is advantageous to maximize it. This approach also limits the space between the object and the NMR sensor to a minimum by using a final pressure lower than the surrounding atmospheric pressure, thus allowing for adherence of the flexible container to the object.

This configuration is important for area systems such as those described in patent U.S. Pat. No. 5,610,522 for which the distance between the NMR system and the measurement volume is rather small (a few centimeters for example).

Figure 2:
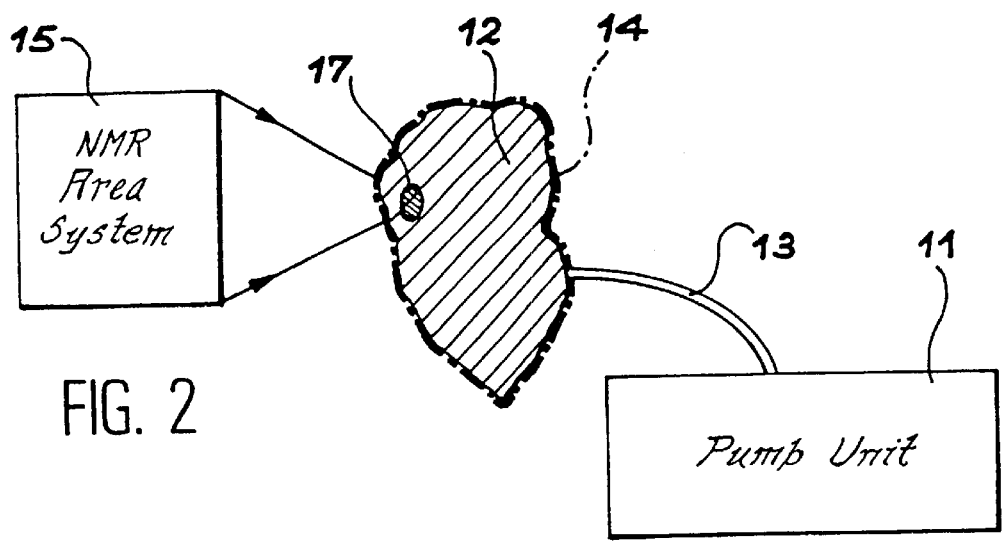
FIG. 2 illustrates a device for characterization of a porous permeable object according to this invention, including a flexible air-tight container and a NMR area system.

FIG. 2 illustrates a device according to the invention including a flexible container 14 adhering to the object 12 to be characterized when the interior of the container is depressurized.

On this figure, reference 11 indicates a pump unit with a gas reserve and a manometer linked to the interior of the flexible container 14 by a pneumatic link 13. Reference 15 indicates a NMR area system during measurement of a given volume 17 of the object 12.

As for a technique developed for the oil industry (see patent U.S. Pat. No. 5,309,098), the use of a NMR area system using CPMG sequences (Carr-Purcell-Meiboom-Gill) allows for determination of average porosity dimensions from the analysis of the signal fall.

Figure 3:
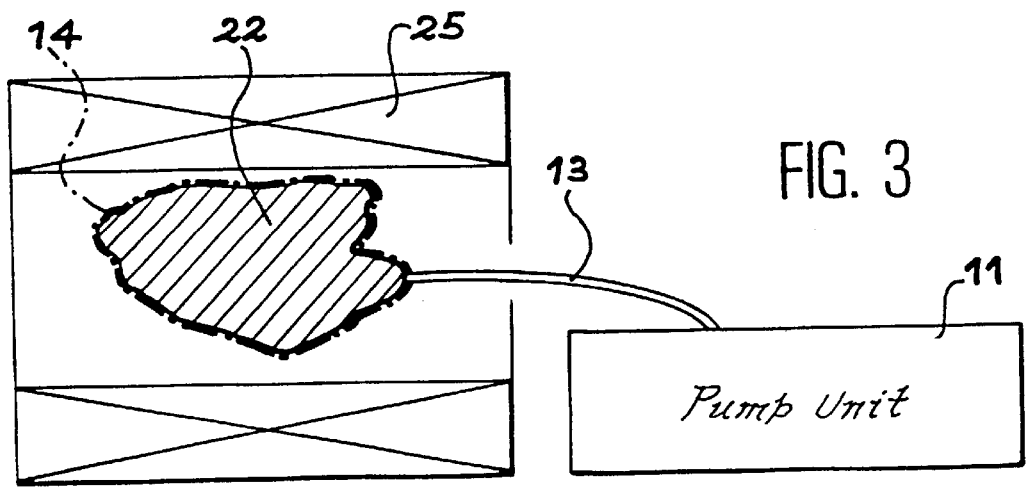
FIG. 3 illustrates a device for characterization of a porous permeable object according to this invention, including a flexible air-tight container and a NMR volume system.

The use of a NMR volume system allows for sweeping of the entire object to be characterized. This case is illustrated by FIG. 3. The object 22 to be characterized is placed in the flexible container 14 linked to the unit 11 by a pneumatic link 13 as for FIG. 2. The entire object 22 enclosed in the flexible container 14 is placed within the NMR volume system 25. This device is usually reserved for small objects.

What is claimed is:

1. A method for characterizing a porous permeable object including the following steps:

placing the object in an air-tight container;

creating a partial vacuum in the container containing the aforesaid object;

measuring the residual pressure in the container in which the partial vacuum is formed;

introducing a quantity of polarized gas into the container having said partial vacuum;

measuring the pressure in the container after introduction of the aforesaid quantity of polarized gas;

determining the density of the polarized gas introduced into the container from the aforesaid pressure measurements;

conducting an NMR measurement of the mass quantity of polarized gas contained in a known volume of the object placed in the air-tight container; and determining of the porosity of the object by calculating the ratio of the mass quantity of polarized gas to the density of the polarized gas introduced into the container.

2. The method according to claim 1, wherein the object is placed in a rigid container.

3. The method according to claim 1, wherein the object is placed in a container which is sufficiently flexible so that depressurization causes the container to adhere to the object.

4. The method according to claim 3, wherein the quantity of polarized gas introduced into the container is such that the container continues to adhere to the object.

5. The method according to claim 1, wherein the step of introduction of a quantity of polarized gas involves introduction of a gas selected from the group consisting of $^3$He and $^{129}$Xe.

6. The method according to claim 1, wherein the NMR measurement is done by an NMR area system.

7. The method according to claim 1, wherein the NMR measurement is done by a system using CPMG sequences, thus allowing for determination of average porosity dimensions.

8. The method according to claim 5, wherein the NMR measurement is done by a system using CPMG sequences, thus allowing for determination of average porosity dimensions.

9. The method according to claim 6, wherein the NMR measurement is done by a system using CPMG sequences, thus allowing for determination of average porosity dimensions.

10. The method according to claim 1, wherein the NMR measurement is done by a NMR volume system.

11. The method according to claim 2, wherein the NMR measurement is done by a NMR volume system.

12. The method according to claim 3, wherein the NMR measurement is done by a NMR volume system.

13. The method according to claim 4, wherein the NMR measurement is done by a NMR volume system.

14. The method according to claim 5, wherein the NMR measurement is done by a NMR volume system.

15. A device for characterizing a porous permeable object including:

an airtight container adaptable to receive the aforesaid object;

means for measurement of the pressure in the airtight container;

means allowing for creation of a partial vacuum in the aforesaid airtight container;

means for introducing a quantity of polarized gas into the depressurized airtight container;

means for NMR measurement of the mass quantity of polarized gas contained in a known volume of the object placed in the airtight container; and means for determination of the density of the polarized gas introduced into the container from data supplied by the means of measurement, and determination of the porosity of the object from measurement of the mass quantity of the polarized gas and the density of the polarized gas introduced into the container.

16. The device according to claim 15, wherein said airtight container is rigid.

17. The device according to claim 15, wherein said airtight container is sufficiently flexible so that the depressurizing causes the container to adhere to the object.

18. The device according to claim 17, wherein said airtight container is sufficiently flexible so that it continues to adhere to the object after introduction of the aforesaid quantity of polarized gas.

19. The device according to claim 15, wherein said means for introducing a quantity of polarized gas are means for introducing a gas selected from the group consisting of $^3$He and $^{129}$Xe.

20. The device according to claim 15, wherein said means of NMR measurement include an NMR area system.

21. The device according to claim 20, wherein said NMR area system is a system which can use CPMG sequences in order to determine the average porosity dimensions.

22. The device according to claim 15, wherein said means of NMR measurement include an NMR volume system.

* * * * *